United States Patent
Keel et al.

(10) Patent No.: US 8,326,422 B2
(45) Date of Patent: Dec. 4, 2012

(54) IMPLANTABLE SYSTEMS AND METHODS FOR MONITORING BNP LEVELS, HF AND MI

(75) Inventors: Allen Keel, San Jose, CA (US); Steve Koh, South Pasadena, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 819 days.

(21) Appl. No.: 12/341,074

(22) Filed: Dec. 22, 2008

(65) Prior Publication Data

US 2010/0160993 A1    Jun. 24, 2010

(51) Int. Cl.
*A61N 1/00* (2006.01)
(52) U.S. Cl. ............. 607/22; 607/17; 607/18; 607/27; 607/28; 600/510
(58) Field of Classification Search ............ 607/17, 607/18, 22, 27, 28; 600/510
See application file for complete search history.

(56) References Cited

U.S. PATENT DOCUMENTS

| | | | |
|---|---|---|---|
| 7,072,715 B1 * | 7/2006 | Bradley | .......... 607/17 |
| 2005/0090719 A1 | 4/2005 | Scheiner et al. | |
| 2006/0276848 A1 | 12/2006 | Min et al. | |
| 2007/0027487 A1 | 2/2007 | Mika et al. | |

OTHER PUBLICATIONS

Bassan, Roberto, et al., "B-type natriuretic peptide: a novel early blood marker of acute myocardial infarction in patients with chest pain and no ST-segment elevation," European Heart Journal 2005, 26:234-240.

McCullough, Peter A., et al., "B-Type Natriuretic Peptide and Clinical Judgment in Emergency Diagnosis of Heart Failure: Analysis From Breathing Not Properly (BNP) Multinational Study," Circulation 2002,106:416-422 available online at http://circ.ahajournals.org/cgi/content/full/106/4/416.

Patel, Jignesh K., et al., "Should we be doing routine biopsy after heart transplantation in a new era of anti-rejection?" Current Opinion in Cardiology 2006, 21:127-131.

* cited by examiner

*Primary Examiner* — Niketa Patel
*Assistant Examiner* — Mallika Fairchild
(74) *Attorney, Agent, or Firm* — Theresa A Raymer; Steven M. Mitchell

(57) ABSTRACT

Methods for monitoring a patient's level of B-type natriuretic peptide (BNP), and implantable cardiac systems capable of performing such methods, are provided. A ventricle is paced for a period of time to provoke a ventricular evoked response, and a ventricular intracardiac electrogram (IEGM) indicative of the ventricular evoked response is obtained. Based on the ventricular IEGM, there is a determination of at least one ventricular evoked response metric (e.g., ventricular evoked response peak-to-peak amplitude, ventricular evoked response area and/or ventricular evoked response maximum slope), and the patient's level of BNP is monitored based on determined ventricular evoked response metric(s). Based on the monitored level's of BNP, the patients heart failure (HF) condition and/or risks and/or occurrences of certain events (e.g., an acute HF exacerbation and/or an acute myocardial infarction) can be monitored.

24 Claims, 4 Drawing Sheets

IMPLANTABLE SYSTEMS AND METHODS FOR MONITORING BNP LEVELS, HF AND MI

FIELD OF THE INVENTION

Embodiments of the present invention relate to implantable cardiac systems, and methods for use therewith.

BACKGROUND

B-type natriuretic peptide (BNP) is a 32-amino-acid polypeptide secreted by the ventricles of the heart in response to excessive stretching of myocytes (heart muscles cells) in the ventricles. The levels of BNP are typically elevated in patients with left ventricular dysfunction. Further, BNP levels correlate with both the severity of symptoms and the prognosis in congestive heart failure. Additionally, BNP appears to be a useful marker of cardiovascular risk, even in people with no clinical evidence of cardiovascular disease.

Levels of BNP are typically measured based on blood samples. For example, 5 mL of blood can be collected into a tube containing potassium EDTA, and the level of BNP can be measured using a Triage™ BNP Test available from Biosite Inc. of San Diego, Calif. However, because most techniques for measuring levels of BNP require blood samples, they are not practical for chronic monitoring of levels of BNP. Nevertheless, it would be advantageous if systems and methods were available for providing chronic monitoring of levels of BNP.

Heart failure (HF) is a condition in which a patient's heart works less efficiently than it should, resulting in the heart failing to supply the body sufficiently with the oxygen rich blood it requires, either at exercise or at rest. Congestive heart failure (CHF) is heart failure accompanied by a build-up of fluid pressure in the pulmonary blood vessels that perfuse the lungs.

Chronic diseases such as CHF require close medical management to reduce morbidity and mortality. Because the disease status evolves with time, frequent physician follow-up examinations are typically necessary. At follow-up, the physician may make adjustments to the drug regimen in order to optimize therapy. This conventional approach of periodic follow-up is unsatisfactory for some diseases, such as CHF, in which acute, life-threatening exacerbations can develop between physician follow-up examinations. Accordingly, it would be advantageous if systems and methods were available for providing chronic monitoring of a patient's HF condition.

Myocardial infraction (MI) (also known as a heart attack) is the death of heart muscle from the sudden blockage of a coronary artery by a blood clot. Coronary arteries are blood vessels that supply the heart muscle with blood and oxygen. Blockage of a coronary artery deprives the heart muscle of blood and oxygen, causing injury to the heart muscle. Injury to the heart muscle causes chest pain and chest pressure sensation. If blood flow is not restored to the heart muscle within 20 to 40 minutes, irreversible death of the heart muscle will begin to occur. Muscle continues to die for six to eight hours at which time the heart attack usually is "complete." The dead heart muscle is eventually replaced by scar tissue. When an MI occurs, it is important that treatment be provide to the patient as soon as possible, so that sustained damage to the patient's heart can be prevented. However, some MIs are silent, meaning they are non-symptomatic, and thus a patient may be unaware that an MI occurred. Further, even if a MI is symptomatic, a patient may not be in a condition that they can notify a physician of the MI.

A goal of the management in of MI is to salvage as much myocardium as possible during the acute phase of MI to prevent further complications. This is because as time passes, the risk of damage to the heart muscle increases. Accordingly, it would be useful if systems and methods were available for chronically monitoring for acute MIs, and risks thereof.

SUMMARY

Certain embodiments of the present invention relate to methods for monitoring a patient's level of BNP, and implantable cardiac systems capable of performing such methods. In accordance with an embodiment, a ventricle is paced for a period of time to provoke a ventricular evoked response, and a ventricular intracardiac electrogram (IEGM) indicative of the ventricular evoked response is obtained. Based on the ventricular IEGM, there is a determination of at least one ventricular evoked response metric, and the patient's level of BNP is monitored based on that determined ventricular evoked response metric(s). Exemplary ventricular evoked response metrics include, but are not limited to, ventricular evoked response peak-to-peak amplitude, ventricular evoked response area and ventricular evoked response maximum slope.

In the manner described above, the ventricular evoked response metric(s) can be determined from time to time (e.g., at different times that ventricular automatic capture threshold detection is performed), so that the patient's level of BNP and/or changes therein, can be monitored over time.

In accordance with specific embodiments, the monitoring of the patient's level of BNP includes estimating a value for the patient's level of BNP based on the determined ventricular evoked response metric(s), e.g., using a quadratic or higher order polynomial equation, but not limited thereto.

In accordance with specific embodiments, a patient's heart failure (HF) condition can be monitored based on the monitored level of BNP, which is/are monitored based on ventricular evoked response metric(s). This can include detecting a worsening of the patient's HF condition if the monitored level of BNP increases, and detecting an improvement of the patient's HF condition if the monitored level of BNP decreases. Additionally, or alternatively, an impending acute HF exacerbation can be predicted based on whether an estimated value of the level of BNP exceeds a threshold, and/or an acute HF exacerbation can be detected based on whether an estimated value of the level of BNP exceeds a threshold. Monitoring a patient's HF condition can also including monitoring changes in the patient's HF condition by monitored changes in the patient's level of BNP.

In accordance with specific embodiments, monitoring for an impending acute MI and/or detection of an acute MI can be performed based on the monitored level of BNP, which is/are monitored based on ventricular evoked response metric(s). This can include detecting an increase in risk of an acute MI if the monitored level of BNP increases, and detecting a decrease in risk of an acute MI if the monitored level of BNP decreases. Additionally, or alternatively, an impending acute MI can be predicted based on whether the monitored level of BNP exceeds a threshold, and/or an occurrence of an acute MI can be detected based on whether an estimated value of the level of BNP exceeds a threshold. Further, changes in a patient's risk of an acute MI can be monitored by monitoring changes in the patient's level of BNP.

Other embodiments of the present invention can be used to select a preferred ventricular pacing energy level. This can include, determining a ventricular capture threshold for pacing a ventricle, and determining, based on the ventricular capture threshold, a first ventricular pacing energy level that provides for reliable capture of the ventricle. For example, the first ventricular pacing energy level can be determined by adding a safety margin, a working margin or some other margin to the determined ventricular capture threshold. At least one ventricular evoked response metric is determined for one or more ventricular evoked response that occurs in response to ventricular pacing at the first ventricular pacing energy level. Additionally, at least one ventricular evoked response is determined for one or more ventricular evoked response that occurs in response to ventricular pacing at one or more energy level greater than the first ventricular pacing energy level. A preferred ventricular pacing energy level to use for ventricular pacing is selected based on the ventricular evoked response metrics determined for the various pacing energy levels. This can include selecting a ventricular pacing energy level greater than the first ventricular pacing energy level as the preferred ventricular pacing energy level, if using the energy level greater than the first ventricular pacing energy level provides at least one of the following: a reduction in the patient's level of BNP, an improved HF condition, a reduction in the patient's risk of an acute HF exacerbation, and/or a reduction in the patient's risk of an acute myocardial infarction.

This summary is not intended to be a complete description of, or limit the scope of, the invention. Alternative and additional features, aspects, and objects of the invention can be obtained from a review of the specification, the figures, and the claims.

DETAILED DESCRIPTION

The following description is of the best modes presently contemplated for practicing various embodiments of the present invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Exemplary Implantable System

Figure 1:
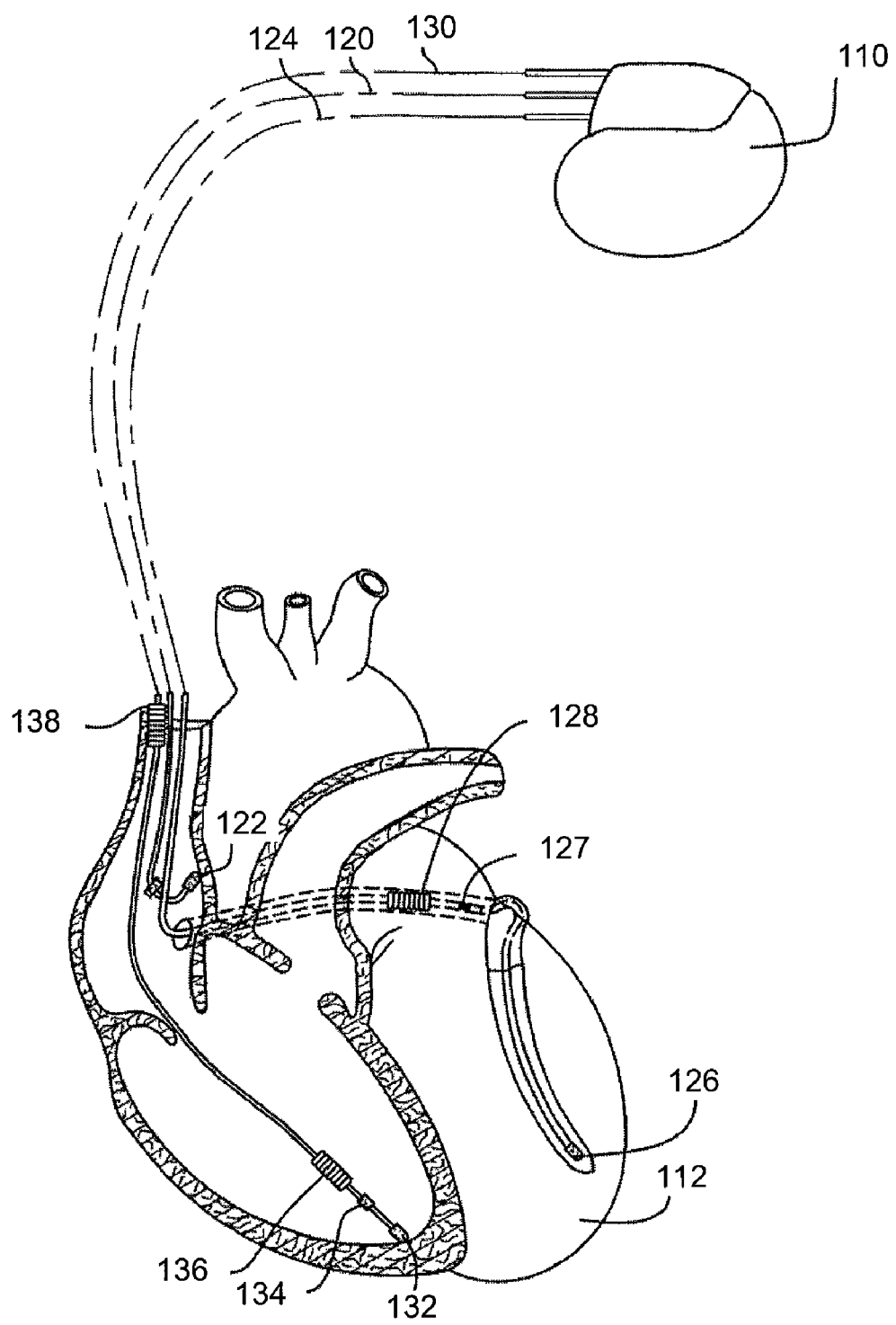
FIG. 1 is a simplified, partly cutaway view illustrating an implantable stimulation device in electrical communication with at least three leads implanted into a patient's heart for delivering multi-chamber stimulation and shock therapy and sensing cardiac activity.

Referring to FIG. 1, an exemplary chronically implantable device 110 (also referred to as a pacing device, a pacing apparatus, a stimulation device, or simply a device) is in electrical communication with a patient's heart 112 by way of three leads, 120, 124 and 130, suitable for delivering multi-chamber stimulation. The device and the leads shall often be referred to hereafter collectively as a chronically implantable system. While not necessary to perform embodiments of the present invention, the exemplary device 110 is also capable of delivering shock therapy.

To sense atrial cardiac signals and to provide right atrial chamber stimulation, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention. More generally, electrodes may be positioned endocardially, epicardially or pericardially.

Figure 2:
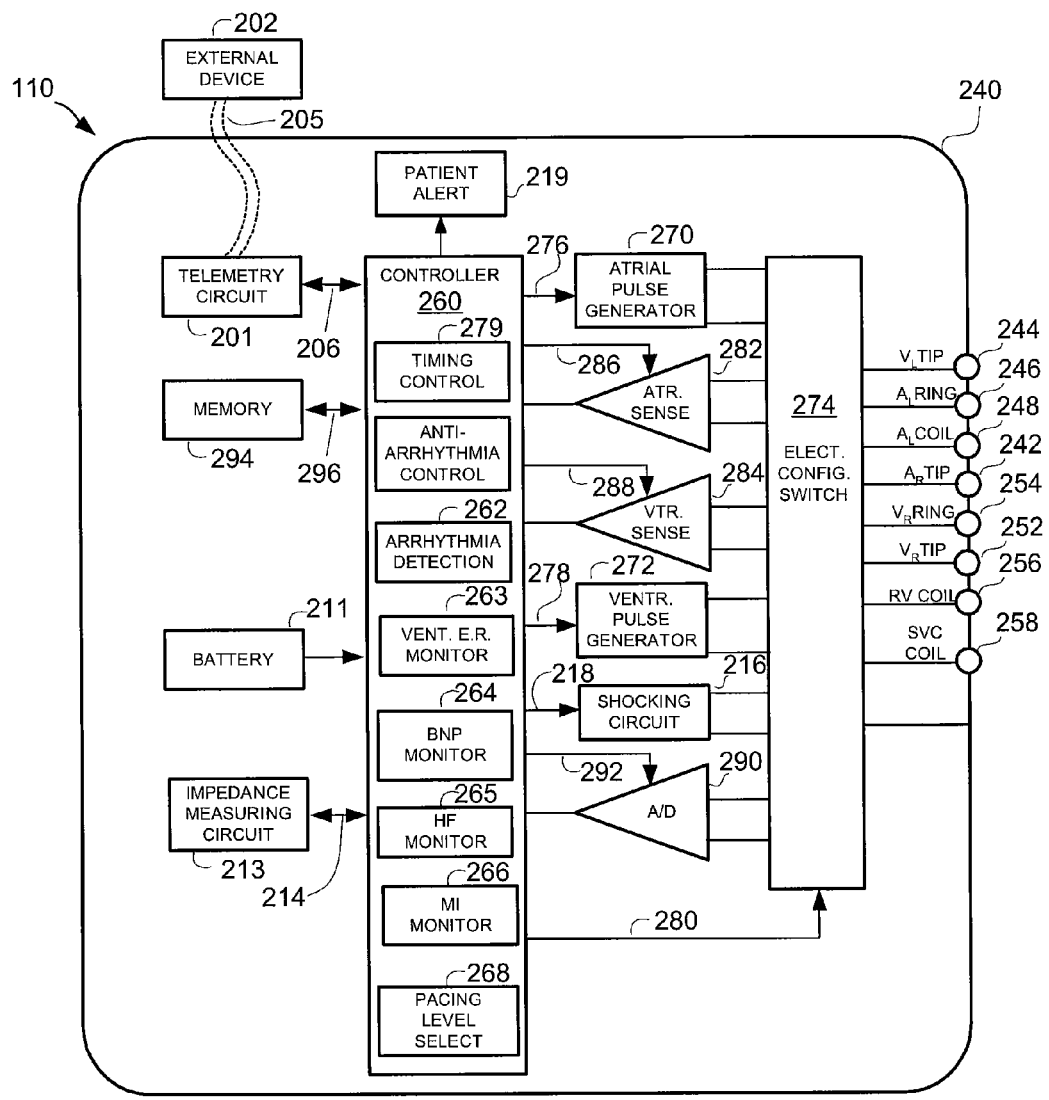
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular tip electrode 126, the left atrial ring electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286. The sensing circuits can be used to acquire IEGM signals, which can be used to measure ventricular evoked response metrics, in accordance with embodiments of the present invention.

For arrhythmia detection, the device 110 includes an arrhythmia detector 262 that utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 262 can be implemented within the microcontroller 260, as shown in FIG. 2. Thus, this detector 262 can be implemented by software, firmware, or combinations thereof. It is also possible that all, or portions, of the arrhythmia detector 262 can be implemented using hardware. Further, it is also possible that all, or portions, of the arrhythmia detector 262 can be implemented separate from the microcontroller 260.

In accordance with embodiments of the present invention, the implantable device 110 includes a ventricular evoked response monitor 263, that can measure ventricular evoked response metrics (i.e., metrics of paced R-waves) of ventricular IEGMs obtained, e.g., using the right ventricular lead 130, but not limited thereto. The ventricular evoked response monitor 263 can be implemented within the microcontroller 260, as shown in FIG. 2. Thus, the ventricular evoked response monitor 263 can be implemented by software, firmware, or combinations thereof. It is also possible that all, or portions, of the monitor 263 can be implemented using hardware. Further, it is also possible that all, or portions, of the ventricular evoked response monitor 263 can be implemented separate from the microcontroller 260. As the term is used herein, a ventricular evoked response is an electrical signal arising from ventricular cardiac tissue depolarization in response to delivery of a ventricular pacing pulse. Stated another way, a ventricular evoked response is a paced ventricular event. The ventricular evoked response monitor 263 can be used to perform step 306, discussed below with reference to FIG. 3.

In accordance with embodiments of the present invention, the implantable device 110 also includes a B-type natriuretic peptide (BNP) monitor 264, that monitors a patient's level of BNP using embodiments of the present invention, which are described in detail below. The BNP monitor 264 can be implemented within the microcontroller 260, as shown in FIG. 2. Thus, the BNP monitor 264 can be implemented by software, firmware, or combinations thereof. It is also possible that all, or portions, of the BNP monitor 264 can be implemented using hardware. Further, it is also possible that all, or portions, of the monitor 264 can be implemented separate from the microcontroller 260. The BNP monitor 264 can include, or communicate with, a component (e.g., ventricular evoked response monitor) that measures ventricular evoked response metrics of a ventricular IEGM. The BNP monitor 264 can be used to perform step 308, discussed below with reference to FIG. 3.

In accordance with embodiments of the present invention, the implantable device 110 also includes a heart failure (HF) monitor 265, that monitors a patient's heart failure condition using embodiments of the present invention, which are described in detail below. The HF monitor 265 can be implemented within the microcontroller 260, as shown in FIG. 2. Thus, the HF monitor 265 can be implemented by software, firmware, or combinations thereof. It is also possible that all, or portions, of the monitor 265 can be implemented using hardware. Further, it is also possible that all, or portions, of the HF monitor 265 can be implemented separate from the microcontroller 260. The HF monitor 265 can include, or communicate with, a component (e.g., the BNP monitor 264) that monitors levels of BNP. The HF monitor 265 can be used to perform step 310, discussed below with reference to FIG. 3.

The implantable device 110 is also shown as including a myocardial infarction (MI) monitor 266 and a pacing energy level selector 268. The MI monitor 266 can predict an impeding acute MI and/or detect an occurrence of an acute MI, in accordance with embodiments of the present invention described below. The pacing energy level selector 268 can select a preferred ventricular pacing energy level, in accordance with embodiments of the present invention described below. The MI monitor 266 and the pacing energy level selector 268 can be implemented by software, firmware, or combinations thereof. It is also possible that all, or portions, of the MI monitor 266 and the pacing energy level selector 268 can be implemented using hardware. Further, it is also possible that all, or portions, of the MI monitor 266 and the pacing energy level selector 268 can be implemented separate from the microcontroller 260. The monitor 266 and/or the selector 268 can communicate with the ventricular evoked response monitor 263, or the MI monitor 266 and/or the pacing energy level selector 268 can monitor ventricular evoked response metrics on their own. The MI monitor 266 can be used to perform step 312, discussed below with reference to FIG. 3. The pacing energy level selector 268 can be used to perform at least some of the steps of FIG. 4, which are discussed below.

The implantable device can also include a patient alert 219, which produces a vibratory or auditory alert, or the like, when triggered. The patient alert 219 can be triggered, e.g., at step 314, discussed below with reference to FIG. 3.

Still referring to FIG. 2, cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy. The memory 294 can also be used to store information about ventricular evoked response metrics and changes in the same can be detected based on the stored information using embodiments of the present invention.

The operating parameters of the implantable device 110 may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. The telemetry circuit 201 can also be used to trigger alarms or alerts of the external device 202, or to instruct the external device 202 to notify a caregiver regarding detection of various episodes, occurrences and changes in conditions that are detected using embodiments of the present invention.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the implantable device 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The above described implantable device 110 was described as an exemplary pacing device. One or ordinary skill in the art would understand that embodiments of the present invention can be used with alternative types of implantable devices. Accordingly, embodiments of the present invention should not be limited to use only with the above described device.

Ventricular Automatic Capture Threshold Detection

The success of a cardiac pacemaker in depolarizing or "capturing" the heart relies on the pacing stimulus energy level delivered to the myocardium exceeding a threshold value, known as the capture threshold. More specifically, the capture threshold represents the amount of electrical energy required to alter the permeability of the myocardial cells to thereby initiate cell depolarization. If the energy of the pacing stimulus does not exceed the capture threshold, then the permeability of the myocardial cells will not be altered and thus no depolarization will result. In contrast, if the energy of the pacing stimulus exceeds the capture threshold, then the permeability of the myocardial cells will be altered such that depolarization will result. The energy is a function of current, voltage and pulse duration (time). Accordingly, the pacing energy level can be adjusted by adjusting one of more of current, voltage and pulse duration.

The capture threshold is not fixed, but rather, may increase and decrease during of the course of a single day, on a daily basis, as well as in response to changes in cardiac disease status. Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. In contrast, if capture occurs consistently at a particular stimulation energy level over a relatively large number of successive stimulation cycles, then it is possible that the capture threshold has decreased such that the stimulation energy is being delivered at level higher than necessary to effect capture. This can be checked by lowering the stimulation energy level and monitoring for capture, or loss of thereof, at the new lower energy level.

To reduce current drain on the power supply, it is desirable to automatically adjust the pacemaker such that the amount of stimulation energy delivered to the myocardium is maintained at a level that will reliably capture the heart without wasting power. Such a process has been called many things, including automatic capture threshold detection, automatic stimulation threshold search, automatic capture verification, automatic verification of capture, and Autocapture™. For the following discussion, this process will be referred to as automatic capture threshold detection.

While there are certainly variations in how and when automatic capture threshold detection can be performed, they all have a similar goal, which is generally to determine whether a delivered pacing stimulus results in stimulation of the myocardium, and, consequently, to adapt the stimulation pulses to a level somewhat above (e.g., a margin above) that which is needed to maintain capture.

Automatic capture threshold detection can be performed when a device is implanted, and from time to time thereafter so that pacing stimulation levels are appropriately adjusted as patient conditions change. For example, an automatic capture threshold detection algorithm can be performed whenever two consecutive pacing pulses fail to evoke capture, and/or may be performed periodically (e.g., every 8 hours, every 24 hours, etc). The following patents, each of which are incorporated herein by reference, provide details of various exemplary automatic ventricular capture threshold detection algorithms: U.S. Pat. No. 7,400,923 (Levine) entitled "Multi-chamber ventricular automatic capture method and apparatus for minimizing true and blanking period induced ventricular undersensing"; U.S. Pat. No. 6,345,201 (Sloman et al.) entitled "System and method for ventricular capture using far-field evoked response."

Depending on the pacing mode that is being used, automatic capture threshold detection can be performed in the atrium and/or in the ventricles. When performed in an atrium, this process can be referred to more specifically as atrial automatic capture threshold detection. Similarly, when performed in a ventricle, this process can be referred to more specifically as ventricular automatic capture threshold detection.

When ventricular automatic capture threshold detection is being performed, the implantable cardiac device monitors for ventricular conduction (i.e., ventricular evoked response, also known as paced R-waves or paced ventricular events) that occur in response to ventricular pacing pulses. Specific embodiments of the present invention take advantage of this process by determining and storing information about (e.g., metrics of) the monitored ventricular evoked responses, such as, but not limited to ventricular evoked response peak-to-peak amplitude, ventricular evoked response area, ventricular evoked response maximum slope, ventricular evoked response maximum amplitude, ventricular evoked response minimum amplitude, ventricular evoked response timing, and/or the dispersion of any of the aforementioned metrics, and use such stored information to monitor levels of BNP and/or perform HF and/or MI monitor based on the monitored levels of BNP. In other words, whenever (or at least some of the times that) a ventricular automatic capture threshold detection process is being performed, one or more ventricular evoked response metric can be measured and stored, and thereafter used for monitoring levels of BNP and/or performing HF and/or MI monitoring based on the monitored levels of BNP. In this manner, specific embodiments of the present invention take advantage of the fact that the ventricular automatic capture threshold detection process will occur from time to time by learning additional information during such process.

B-type Natriuretic Peptide (BNP) Monitoring

Figure 3:
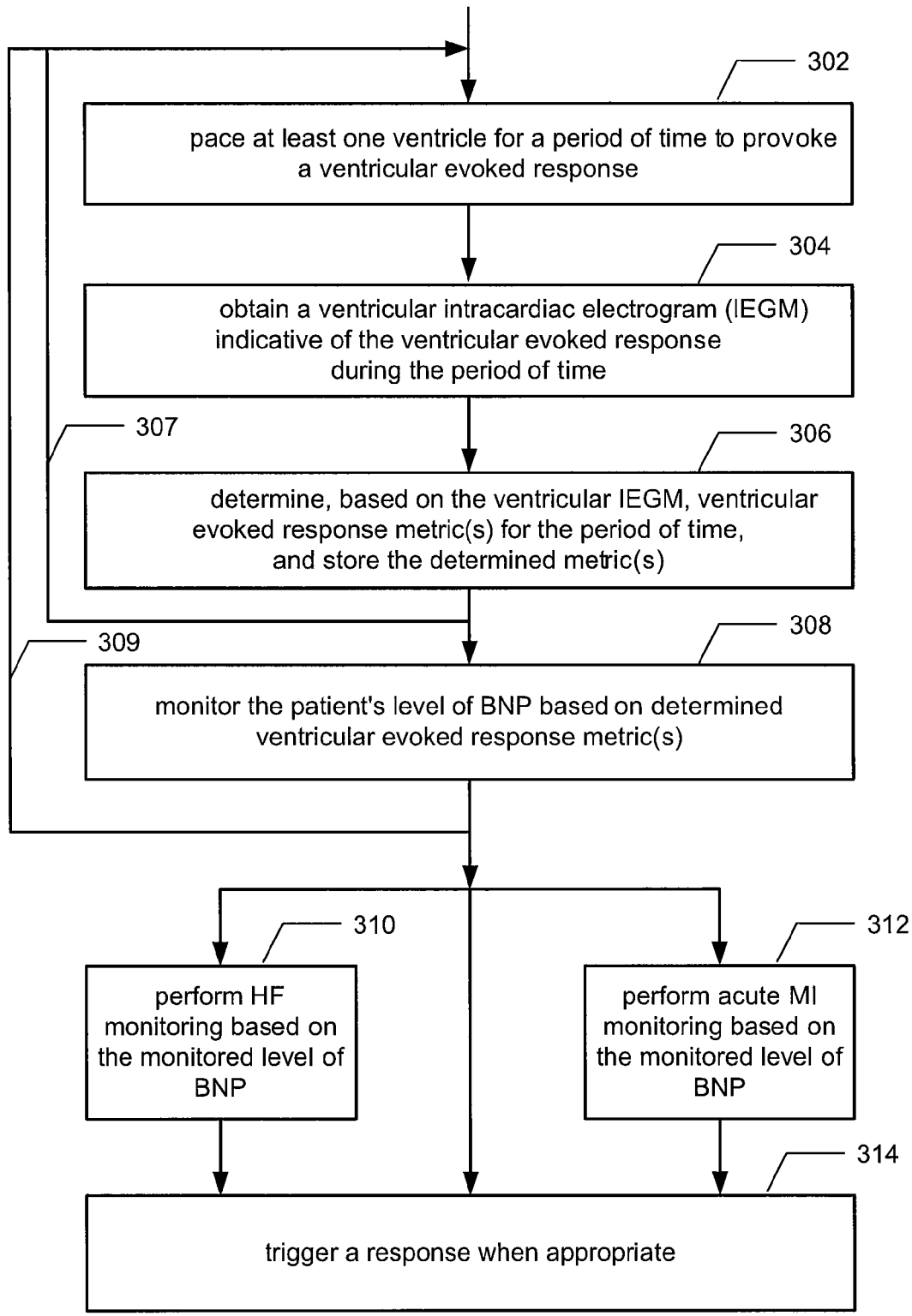
FIG. 3 is a high level flow diagram that is used to summarize specific embodiments of the present invention that can be used to monitor a patient's level of BNP and monitor changes in a patient's level of BNP, as well as to perform HF and/or MI monitoring based on the monitored levels of BNP.

The high level flow diagram of FIG. 3 will now be used to describe methods for use by an implanted system including an implanted cardiac device and at least one implanted lead, for monitoring a patient's level of BNP. Embodiments of the present invention are also directed to chronically implanted systems that can implement such methods.

Referring to FIG. 3, at step 302, at least one ventricle is paced for a period of time to provoke a ventricular evoked response. At step 304, a ventricular intracardiac electrogram (IEGM) is obtained, which is indicative of the ventricular evoked response during the period of time that the at least one ventricle is being paced. Steps 302 and 304 can be accomplished using the implantable cardiac device 110 and the right ventricular lead 130, which were discussed above with reference to FIGS. 1 and 2, but embodiments of the present invention should not be limited thereto.

At step 306, based on the ventricular IEGM there is a determination of ventricular evoked response metric(s) indicative of ventricular electrical activity during the period of time, and information about such ventricular evoked response metric(s) is stored, e.g., in memory 294 of FIG. 2. Metrics of ventricular evoked response that can be measured from the ventricular IEGM, include, e.g., ventricular evoked response peak-to-peak amplitude, ventricular evoked response area, ventricular evoked response maximum slope, ventricular evoked response maximum amplitude (ventricular evoked response max), ventricular evoked response minimum amplitude (ventricular evoked response min), ventricular evoked response timing, and/or the dispersion of any of the aforementioned metrics. For example, ventricular evoked response peak-to-peak amplitude dispersion can be the difference between the maximum ventricular evoked response peak-to-peak amplitude and the minimum ventricular evoked response peak-to-peak amplitude (i.e., the range of peak-to-peak amplitudes). The dispersion of another one of the other above mentioned metrics can alternatively or additionally be used. Also, other measures of dispersion besides range can be used, e.g., standard deviation, interquartile range, mean difference, median absolute deviation, average absolute deviation (or simply average deviation), coefficient of variation, quartile coefficient of dispersion, relative mean difference, variance (the square of the standard deviation) or variance-to-mean ratio. Step 306 can be performed, e.g., by the ventricular evoked response monitor 263 of FIG. 2, but is not limited thereto.

Preferably, the ventricular evoked response metric(s) that are determined at step 306, each time step 306 is repeated, is/are of the same type, so that such metric(s) can be readily compared. For example, each time step 306 is performed a ventricular evoked response peak-to-peak amplitude and a ventricular evoked response area for 60 cardiac cycles can be determined.

Preferably each period of time referred to in steps 302, 304 and 306 spans a plurality of cardiac cycles, so that ventricular evoked response metric(s) is/are determined for each of a plurality of cardiac cycles, and metrics of the same type (e.g., ventricular evoked response peak-to-peak amplitude) are combined, e.g., averaged, summed, filtered (according to signal stability and/or quality), heart rate corrected, or the like, to reduce the affects of noise and motion artifacts on such measurements. For example, the ventricular evoked response peak-to-peak amplitude for 60 cardiac cycles can be measured and averaged to produce the ventricular evoked response peak-to-peak amplitude for a period of time lasting 60 cardiac cycles. Additionally, or alternatively, a ventricular evoked response area and/or ventricular evoked response maximum slope for the same 60 cardiac cycles can be measured and averaged to produce the ventricular evoked response area and/or the ventricular evoked response maximum slope. Accordingly, in this example, the result of step 306 can be a ventricular evoked response peak-to-peak amplitude, a ventricular evoked response area and/or a ventricular evoked response maximum slope, for the period of time (e.g., for a period of time lasting 60 cardiac cycles).

At step 308, the patient's level of BNP is estimated based on at least one ventricular evoked response metric determined at step 306. This can be accomplished, e.g., by plugging one or more ventricular evoked response metric (determined at step 306) into an algorithm or other model that converts such metrics to estimates of BNP. Such an algorithm or model can be determined during a calibration procedure during which actual measures of BNP (e.g., from blood samples) and ventricular evoked response metric(s) are measured simultaneously. In accordance with specific embodiments, a quadratic or higher order polynomial equation can be used to estimate the patient's level of BNP. For example, the following equation can be used:

$$erBNP = k_1 * ER^2 + k_2 ER + b,$$

where $k_1$, $k_2$, and b are constants determined from a quadratic fit, ER is a measured ventricular evoked response metric, and erBNP is the unknown level of BNP being estimated based on the measured ventricular evoked response metric.

The above equation can also be expanded for use with various different types of ventricular evoked response metrics.

In accordance with an embodiment of the present invention, a calibration (e.g., an initial calibration) can be performed using the following equation $$erBNP = \left(\frac{highBNP - lowBNP}{highER - lowER}\right)(ER - highER) + highBNP$$

where erBNP is the unknown level of BNP whose value is being estimated,

ER is the ventricular evoked response metric corresponding to the unknown level of BNP, highBNP is a high measured BNP level, lowBNP is a low measured BNP level, highER is the ventricular evoked response metric corresponding to the highBNP, and lowER is the ventricular evoked response metric corresponding to the lowBNP.

The high measured BNP level (i.e., highBNP) and the ventricular evoked response metric corresponding to the highBNP (i.e., highER) can be measured, e.g., when a patient is initially admitted to a hospital for a condition that corresponds to a high BNP level (e.g., an HF exacerbation or an acute MI). The low measured BNP level (i.e., lowBNP) and the ventricular evoked response metric corresponding to the lowBNP (i.e., lowER) can be measured, e.g., post-treatment for the condition, but prior to discharge. The highBNP and lowBNP values can be measured from blood samples take from the patient, e.g., using a Triage™ BNP Test available from Biosite Inc. of San Diego, Calif., or using an i-STAT Analyzer™ and BNP Cartridge available from Abbott Laboratories of Abbott Park, Ill., but not limited thereto. The highER and lowER metrics can be measured using the cardiac device implanted within the patient, i.e., the same device that can thereafter be used to estimate a value of the level of BNP based on ventricular evoked response metric(s).

Steps 302, 304 and 306 can be repeated from time to time, as indicated by arrow 307 (or arrow 309). In other words, steps 302, 304 and 306 can be performed for each of a plurality of periods of time. For examples, steps 302, 304 and 306 can be performed for 60 seconds or 60 cardiac cycles, and repeated every 10 minutes, hour, day, or the like. Each time steps 302, 304 and 306 are preformed, a patient's level of BNP can be monitored (e.g., a value estimated) at step 308. As these steps are repeated, changes in the patient's level of BNP can be monitored based on the changes in the levels of BNP estimated at step 308. Step 308 can be performed, e.g., by the BNP monitor 264 of FIG. 2, but is not limited thereto.

Levels of BNP need not be estimated at step 308, but rather, as steps 302, 304 and 306 are repeated from time to time, changes in the levels of BNP can be monitored at step 308 based on the changes in the metric(s) of ventricular evoked response determined at step 306. For example, if it is determined that there is a positive correlation between a specific metric of ventricular evoked response and level of BNP, if that metric increases over time, then at step 308 there can be a determination that the level of BNP has increased over time. This is just an example, which is not meant to be limiting.

In specific embodiments, steps 302, 304 and 306 (and optionally step 308) are only performed when certain pre-conditions are satisfied, e.g., there is consistent capture, there is a specific pacing rate, specific pacing energy level, specific patient posture and/or the patient is at rest. Additional and/or alternative pre-conditions are also possible, and within the scope of the present disclosure. In such embodiments, the device can be programmed to periodically perform these steps to (e.g., every four hours), but only if the pre-conditions are satisfied. If the pre-conditions are not satisfied, the device can wait until they are satisfied to perform the steps, or the device can skip the performing of the steps. By only determining levels of BNP (and/or changes therein) when certain pre-conditions are satisfied, there is a good chance that detected changes in BNP are not simply due to changes in such conditions (e.g., due to changes in pacing rate and/or pacing energy level).

Whenever steps 302, 304 and 306 are preformed, a patient's level of BNP can be determined at step 308. Alternatively, as mentioned above, steps 302, 304 and 306 may be performed multiple times before step 308 is performed (e.g., in which case, changes in a patient's level of BNP may be determined at step 308). For example, at step 308, a change in the at least one ventricular evoked response metric over time can be detected based on the information stored at various instances of step 306. Such a change can be an increase, a decrease, or there can be relatively no change. A magnitude of the change can also be determined. For example, at step 308 a ventricular evoked response peak-to-peak amplitude for a second period of time can be compared to a ventricular evoked response peak-to-peak amplitude for a first period of time. Additionally, or alternatively, a ventricular evoked response area for the second period of time can be compared to the ventricular evoked response area for the first period of time. Where multiple ventricular evoked response metrics are to be compared at step 308, weighting factors can be used to combine the ventricular evoked response metrics or combine the results of multiple comparisons.

At step 308, a change in a patient's level of BNP can be monitored based on the detected change in the at least one ventricular evoked response over time. Step 308 can include determining whether a patient's level of BNP has increased, decreased, or stayed relatively the same. This can include interpreting an increase in a certain ventricular evoked response metric, such as ventricular evoked response peak-to-peak amplitude and/or ventricular evoked response area, as being indicative of increased level of BNP, and interpreting decreases in the same ventricular evoked response metric as being indicative of decreases in level of BNP. Relatively no change in a ventricular evoked response metric can be interpreted in relatively no change in level of BNP. Alternative ventricular evoked response metrics may be used. How to interpret increases or decreases in alternative ventricular evoked response metrics depends on the metric, and can be determined through experimentation, e.g., from empirical data. For example, some ventricular evoked response metrics (such a ventricular evoked response peak-to-peak amplitude) have a positive correlation with level of BNP, while others have a negative correlation.

HF Monitoring

As described above in the Background, chronic diseases such as CHF require close medical management to reduce morbidity and mortality. However, the conventional approach of periodic patient follow-ups has proved unsatisfactory, as life-threatening exacerbations can develop between physician follow-up examinations. Further, if a developing HF exacerbation is recognized early, it can be more easily and inexpensively terminated, typically with a modest increase in oral diuretic. However, if it develops beyond the initial phase, an acute HF exacerbation becomes difficult to control and terminate. Hospitalization in an intensive care unit is often required. It is during an acute exacerbation of heart failure that many patients succumb to the disease.

Further, it is often difficult for patients to recognize a developing HF exacerbation, despite the presence of numerous physical signs that would allow a physician to readily detect it. Furthermore, since exacerbations typically develop over hours to days, even frequently scheduled routine follow-up with a physician cannot effectively detect most developing exacerbations. It is therefore desirable to have a system that allows for routine, frequent monitoring of patients so that an exacerbation can be recognized early in its course. With the patient and/or physician thus notified by the monitoring system of the need for medical intervention, a developing exacerbation can more easily and inexpensively be terminated early in its course.

As indicated at step 310, a patient's HF condition can be monitored based on the patient's level of BNP monitored at step 308. This can include interpreting an increase in a patient's level of BNP as being indicative of a worsening HF condition and/or an increased risk of an acute HF exacerbation, and interpreting decreases in the patient's level of BNP as being indicative of an improved HF condition and/or a reduced risk of an acute HF exacerbation. Relatively no change in the patient's level of BNP can be interpreted as relatively no change in the HF condition and/or relatively no change in the risk of an acute HF exacerbation. The term "based on", as used herein, means based at least in part on (unless otherwise specified), meaning that other factors can be used in a determination or decision. For example, the patient's HF condition can be monitored based on the patient's level of BNP, as well as on (e.g., in combination with) other factors or determinations.

Additionally, or alternatively, step 310 can include predicting an impending acute HF exacerbation based on whether the estimated level of BNP exceeds a first threshold, and/or whether the estimated level of BNP exceeds a second threshold can be used to detect an acute HF exacerbation. The term "impending" can mean, e.g., within a month, but is not limited thereto. The first threshold and the second threshold, may or may not be the same. The threshold(s) can be set as a percentage of the patient's high BNP value, e.g., 80% of the high BNP value. Such thresholds can be determined, e.g., using empirical data collected over time for the patient and/or for a patient population, but is not limited thereto. As will be described below, with reference to step 314, an appropriate response can be triggered when an impending acute HF exacerbation is predicted and/or an acute HF exacerbation is detected.

At step 314, a response can be triggered if an estimated value for the patient's level of BNP (an increase in the patient's level of BNP) exceeds a specified threshold. Alternatively, or additionally, at step 314 a response can be triggered if a change in the at least one ventricular evoked response metric is in a direction indicative of an increase in the patient's level of BNP beyond a specified threshold.

If it is determined at step 310 that the patient's level of BNP has increased beyond a specified threshold (and thus, e.g., that a patient has a heightened risk of an acute HF exacerbation, and/or that the patient's HF condition has worsened beyond a specified threshold, or it is believed that an acute HF exacerbation has been detected), then at step 314 an appropriate therapy can be triggered. One type of therapy would be for an implanted device, if appropriately equipped, to deliver appropriate drug therapy. In another embodiment, the implantable device can perform appropriate pacing therapy to attempt to prevent and/or treat an acute heart failure exacerbation. One of ordinary skill in the art would understand from the above description that other responses are also possible, while still being within the spirit and scope of the present invention.

Additionally or alternatively, a patient can be alerted (e.g., using alert 219) at step 314 if it was determined at step 310 that the patient's level of BNP exceeded a specific threshold (and thus, e.g., that a patient has a heightened risk of an acute HF exacerbation, and/or that the patient's HF condition has worsened beyond a specified threshold, or it is believed that an acute HF exacerbation has been detected). An alert could be a vibratory or auditory alert that originates from within the implantable device 110. Alternatively, the implantable device 110 may wirelessly transmit an alert to an external device (e.g., 202) that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible an HF exacerbation may be avoided, or if it does occur, the patient will be less dangerous to themselves and others if the patient is resting when the exacerbation occurs (as opposed, e.g., to driving a car). It is also possible that the alert can be generated by an external device (e.g., 202).

Additionally or alternatively, the patient can be instructed to take medication when alerted. Additionally or alternatively, a caregiver (e.g., physician) can be alerted if it is determined that the patient's level of BNP, or an increase therein, beyond a threshold (and thus, e.g., that a patient has a heightened risk of an acute HF exacerbation, and/or that the patient's HF condition has worsened beyond a specified threshold and/or that it is believed that an acute HF exacerbation has been detected). Additionally or alternatively, information related to ventricular evoked response metric(s) and/or changes therein can be stored. This can include, for example, storing information related to ventricular evoked response peak-to-peak amplitude, ventricular evoked response area and/or ventricular evoked response maximum slope, but is not limited thereto. Additionally, or alternatively, estimated values of levels of BNP can be stored. If such information is stored in an implanted device, such information can be continually, or from time to time, automatically uploaded to an external device (e.g., 202). Such an external device 202 can be located, e.g., in the patient's home, and the information can be transmitted (e.g., through telephone lines or the Internet) to a medical facility where a physician can analyze the information. For example, the external device 202 can be a bedside monitor, or an ambulatory device that the patient carries with them. Alternatively, the external device 202 can be an external programmer located at a medical facility, and the information can be uploaded when the patient visits the facility.

MI Monitoring

As described above in the Background, there are numerous reasons why it would be useful if systems and methods were available for chronically monitoring for acute MIs, and risks thereof.

As indicated at step 312, acute MI monitoring can be performed based on the patient's level of BNP monitored at step 308. This can include interpreting an increase in a patient's level of BNP as being indicative of an increased risk of an acute MI, and interpreting decreases in the patient's level of BNP as being indicative of a reduced risk of an acute MI. Relatively no change in the patient's level of BNP can be interpreted in relatively no change in the risk of an acute MI.

Additionally, or alternatively, step 312 can include predicting an impending acute MI based on whether the estimated level of BNP exceeds a first threshold, and/or whether the estimated level of BNP exceeds a second threshold can be used to detect an acute MI occurrence. The term "impending" can mean, e.g., within a month, but is not limited thereto. The first threshold and the second thresholds, may or may not be the same. The threshold(s) can be set as a percentage of the patient's high BNP value, e.g., 75% of the high BNP value. Such thresholds can be determined, e.g., using empirical data collected over time for the patient and/or for a patient population, but is not limited thereto. As will be described below, with reference to step 314, an appropriate response can be triggered when an impending acute MI is predicted and/or an acute MI is detected.

If it is determined at step 312 that the patient's level of BNP has increased beyond a specified threshold (and thus, e.g., that a patient has a heightened risk of an acute MI and/or that an impending acute MI is predicted, or it is believed that an acute MI has been detected), then at step 314 an appropriate therapy can be triggered. One type of therapy would be for an implanted device, if appropriately equipped, to deliver appropriate drug therapy. In another embodiment, the implantable device can perform appropriate pacing therapy to attempt to treat an acute MI. One of ordinary skill in the art would understand from the above description that other responses are also possible, while still being within the spirit and scope of the present invention.

Additionally or alternatively, a patient can be alerted (e.g., using alert 219) at step 314 if it was determined at step 310 that the patient's level of BNP exceeded a specific threshold (and thus, e.g., that there is a detection of a heightened risk of an acute MI and/or that an impending acute MI is predicted, or it is believed that an acute MI has been detected). An alert could be a vibratory or auditory alert that originates from within the implantable device 110. Alternatively, the implantable device 110 may wirelessly transmit an alert to an external device (e.g., 202) that produces a visual or auditory alert that a patient can see or hear. The alert may inform that patient that he should rest, or if the patient is operating some type of dangerous machinery (e.g., a car), that the patient should stop what they are doing. By alerting the patient to rest, the patient will be less dangerous to themselves and others if the patient is resting when the acute MI occurs (as opposed, e.g., to driving a car). It is also possible that the alert can be generated by an external device (e.g., 202).

Additionally or alternatively, the patient can be instructed to take medication when alerted. Additionally or alternatively, a caregiver (e.g., physician) can be alerted if it is determined that the patient's level of BNP, or an increase therein, beyond a threshold (and thus, e.g., that there is a detection of a heightened risk of an acute MI and/or that an impending acute MI is predicted, or it is believed that an acute MI has been detected). Additionally or alternatively, information related to ventricular evoked response metric(s) and/or changes therein can be stored. This can include, for example, storing information related to ventricular evoked response peak-to-peak amplitude, ventricular evoked response area and/or ventricular evoked response maximum slope, but is not limited thereto. Additionally, or alternatively, estimated values of levels of BNP can be stored. If such information is stored in an implanted device, such information can be continually, or from time to time, automatically uploaded to an external device (e.g., 202). Such an external device 202 can be located, e.g., in the patient's home, and the information can be transmitted (e.g., through telephone lines or the Internet) to a medical facility where a physician can analyze the information. For example, the external device 202 can be a bedside monitor, or an ambulatory device that the patient carries with them. Alternatively, the external device 202 can be an external programmer located at a medical facility, and the information can be uploaded when the patient visits the facility.

Ventricular Pacing Energy Level

Specific embodiments of the present invention relate to selecting a preferred ventricular pacing energy level. As briefly discussed above, a goal of ventricular automatic capture threshold detection is to adjust the stimulation energy delivered to a ventricle so that it is at a level that will reliably capture the ventricle without wasting energy. This is typically accomplished by determining, from time to time, the ventricular capture threshold level and pacing the ventricle at a level equal to the ventricular capture threshold level, or more likely, equal to the ventricular capture threshold level plus a specified margin, e.g., a safety margin or working margin. A safety margin can be defined, e.g., as a ratio (e.g., 2:1 or 3:1) or percentage (e.g., 150% or 200%) relative to the measured ventricular capture threshold. A working margin can be defined, e.g., as a fixed amount (e.g., 0.25V) added to the measured ventricular capture threshold. Typically, a device will pace a ventricle at the capture threshold plus the specified margin, not taking into account other factors. In contrast, in accordance with the embodiments of the present invention described with reference to FIG. 4, ventricular pacing may occur at a somewhat higher level if the result is a reduction in the patient's level of BNP, an improved HF condition, a reduced risk of an HF exacerbation, and/or a reduced risk of an acute MI.

Figure 4:
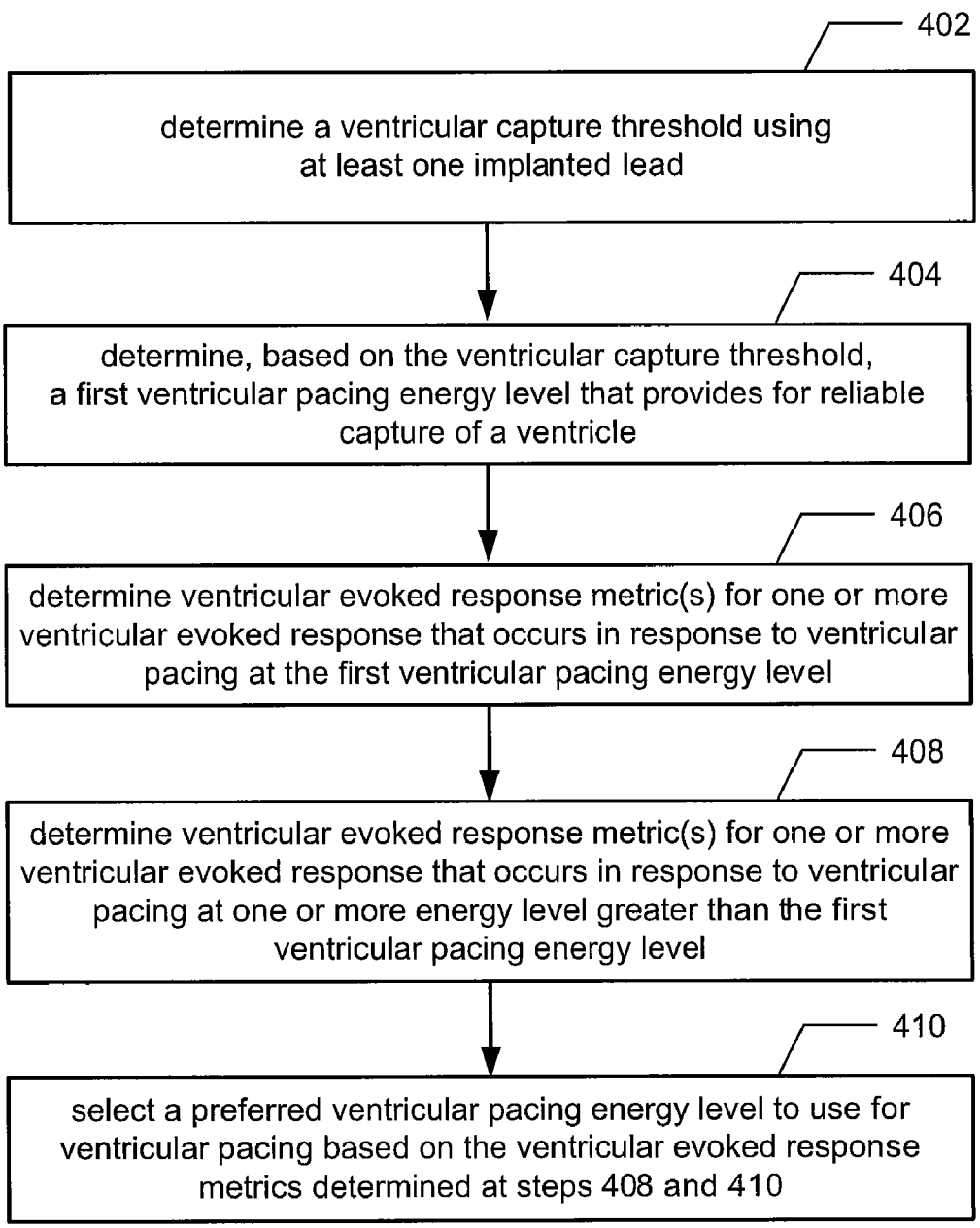
FIG. 4 is a high level flow diagram that is used to summarize specific embodiments of the present invention that can be used to select a pacing energy level taking into account whether an increased energy level results in a reduction in level of BNP, an improved HF condition, a reduced risk of an acute HF exacerbation and/or reduced risk of an acute MI.

Referring to FIG. 4, at a step 402, a ventricular capture threshold for pacing in a ventricle is determined using at least one implanted lead. As explained above, the ventricular capture threshold represents the amount of electrical energy required cause ventricular depolarization. There are various well known ways to determine the ventricular capture threshold, and thus, this step need not be described in additional detail.

At step 404, a first ventricular pacing energy level that provides for reliable capture of a ventricle is determined based on the ventricular capture threshold determined at step 402. As was discussed above, this energy level can be the ventricular capture threshold level, or the ventricular capture threshold level plus a specified margin, e.g., a safety or working margin.

At step 406, at least one ventricular evoked response metric is determined for one or more ventricular evoked response (also known as a paced ventricular event) that occurs in response to ventricular pacing at a first energy level specified based on the determined ventricular capture threshold. As was discussed above with reference to FIG. 3, exemplary ventricular evoked response metrics that can be measured include ventricular evoked response maximum amplitude, ventricular evoked response minimum amplitude, ventricular evoked response peak-to-peak amplitude, ventricular evoked response duration, ventricular evoked response area, ventricular evoked response maximum slope, and ventricular evoked response timing, and/or the dispersion of any of the aforementioned metric. Preferably such ventricular evoked response metric(s) is/are determined for a plurality of paced ventricular events that occurs in response to ventricular pacing at the first ventricular pacing energy level, and the metrics are combined, e.g., averaged, summed, or the like, to reduce the affects of noise and motion artifacts on such measurements.

At step 408, at least one ventricular evoked response metric is determined for one or more ventricular evoked response (also known as a paced ventricular event) that occurs in response to ventricular pacing at one or more energy level greater than the first ventricular pacing energy level. For example, the one or more energy level (greater than the first ventricular pacing energy level) can be one or more percentage of the first ventricular pacing energy level (e.g., 110%, 120% and 130% of the first ventricular pacing energy level), or one or more fixed voltage level above the first ventricular pacing energy level (e.g., 0.25V, 0.50V and 0.75V). These are just a few examples, which are not meant to be limiting.

The determining of the at least one ventricular evoked response metric at step 406 can occur during the determining of the ventricular capture threshold at step 402, e.g., if energy levels above the actual capture threshold are tested during the search for the ventricular capture threshold. Similarly, the determining of the at least one ventricular evoked response metric at step 408 can occur during the determining of the ventricular capture threshold at step 402, e.g., if energy levels above the actual capture threshold and above the first ventricular pacing energy level are also tested during the search for the ventricular capture threshold.

At step 410, a preferred ventricular pacing energy level to use for ventricular pacing is determined (e.g., selected) based on the ventricular evoked response metrics determined at steps 406 and 408. At step 410 a ventricular pacing energy level greater than the first ventricular pacing energy level (determined at step 404) can be selected as the preferred ventricular pacing energy level, if it is determined based on ventricular evoked response metrics (determined at step 406 and 408) that pacing at an energy level greater than the first ventricular pacing energy level would reduce the patient's level of BNP, improve the patient's HF condition and/or reduce the patient's risk of an HF exacerbation and/or reduce the patient's risk of acute MI. Exemplary techniques for determining the patient's level of BNP, HF condition and/or risk of acute HF exacerbation and/or risk of acute MI based on levels of BNP determined from ventricular evoked response metric(s) were discussed above with reference to FIG. 3.

In the embodiment of FIG. 4, a pacing energy level that is higher than is necessary for reliable capture may be selected if the higher energy level provides for a reduction in level of BNP, an improved HF condition and/or a lower risk of an acute HF exacerbation and/or a lower risk of an acute MI. The extent of the reduction in the patient's level of BNP, the improvement in HF condition and/or the extent of the reduction in risk of an acute HF exacerbation and/or the extent of the reduction in risk of an acute MI can be used to determine whether it's worth increasing the pacing energy level, because the higher the pacing energy level the shorter the battery life. Various algorithms can be developed that enable a cardiac device to make such decisions, e.g., based on programmed preferences of a physician. Alternatively, a physician can make such a determination.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for monitoring a patient's level of B-type natriuretic peptide (BNP), for use by an implanted system including an implanted cardiac device and at least one implanted lead, the method comprising:
    (a) pacing at least one ventricle for a period of time to provoke a ventricular evoked response;
    (b) obtaining a ventricular intracardiac electrogram (IEGM) indicative of the ventricular evoked response during the period of time;
    (c) determining, based on the ventricular IEGM, at least one ventricular evoked response metric for the period of time; and
    (d) monitoring the patient's level of BNP based on at least one ventricular evoked response metric determined at step (c), wherein monitoring the patient's level of BNP includes: estimating a patient's level of BNP or estimating a change in the patient's level of BNP.

2. The method of claim 1, wherein:
    steps (a), (b) and (c) are repeated at different times that a set of pre-conditions are satisfied; and
    step (d) can be performed every time step (c) is performed, or step (d) can be performed once for a plurality of times that step (c) is performed.

3. The method of claim 2, wherein step (d) comprises monitoring changes in the patient's estimated level of BNP by monitoring changes in the at least one ventricular evoked response metric determined at step (c).

4. The method of claim 1, wherein step (d) comprises estimating a patient's level of BNP by estimating a value for the patient's level of BNP based on at least one ventricular evoked response metric determined at step (c).

5. A method for monitoring a patient's level of B-type natriuretic peptide (BNP), for use by an implanted system including an implanted cardiac device and at least one implanted lead, the method comprising:
- (a) pacing at least one ventricle for a period of time to provoke a ventricular evoked response;
- (b) obtaining a ventricular intracardiac electrogram (IEGM) indicative of the ventricular evoked response during the period of time;
- (c) determining, based on the ventricular IEGM, at least one ventricular evoked response metric for the period of time; and
- (d) monitoring the patient's level of BNP based on at least one ventricular evoked response metric determined at step (c), wherein steps (a), (b) and (c) are performed for each of a plurality of periods of time, and during the plurality of periods of time:

step (a) includes
- pacing the at least one ventricle to provoke a ventricular evoked response while the patient has a low level of BNP (lowBNP);
- pacing the at least one ventricle to provoke a ventricular evoked response while the patient has a high level of BNP (highBNP); and
- pacing the at least one ventricle to provoke a ventricular evoked response while the patient has an unknown level of BNP;

step (c) includes
- determining a ventricular evoked response metric (lowER) corresponding to the low BNP;
- determining a ventricular evoked response metric (highER) corresponding to the high BNP; and
- determining a ventricular evoked response metric (ER) corresponding to the unknown level of BNP; and step (d) includes estimating the value for the unknown level of BNP using the following equation:

$$erBNP = \left(\frac{highBNP - lowBNP}{highER - lowER}\right)(ER - highER) + highBNP$$

where
- erBNP is the unknown level of BNP whose value is being estimated,
- ER is the ventricular evoked response metric corresponding to the unknown level of BNP,
- highBNP is a high measured BNP level,
- lowBNP is a low measured BNP level,
- highER is the ventricular evoked response metric corresponding to the highBNP, and
- lowER is the ventricular evoked response metric corresponding to the lowBNP.

6. The method of claim 5, wherein:
- the highBNP is measured from a blood sample when the patient visits a facility for a condition that typically results in a high level of BNP; and
- the lowBNP is measured from a blood sample after treatment for the condition, prior to the patient leaving the facility.

7. The method of claim 4, wherein steps (a), (b) and (c) are performed for each of a plurality of periods of time, and step (d) comprises using a quadratic or higher order polynomial equation to estimate the value for the patient's level of BNP.

8. The method of claim 4, wherein step (d) comprises estimating the value for the patient's level of BNP using the following equation:

$$erBNP = k_1 * ER^2 + k_2 ER + b,$$

where
- $k_1$, $k_2$, and b are constants determined from a quadratic fit,
- ER is a ventricular evoked response metric determined at step (c), and
- erBNP is an unknown level of BNP whose value is being estimated.

9. The method of claim 1, wherein step (d) comprises estimating a patient's level of BNP by estimating a value for the patient's level of BNP based on at least one ventricular evoked response metric determined at step (c); and
further comprising:
- (e) monitoring the patient's heart failure (HF) condition based on the patient's estimated level of BNP estimated at step (d).

10. The method of claim 9, wherein step (e) includes:
- detecting a worsening of the patient's HF condition if the estimated level of BNP increases; and
- detecting an improvement of the patient's HF condition if the estimated level of BNP decreases.

11. The method of claim 9, wherein step (e) includes at least one of the following:
- predicting an impending acute HF exacerbation based on whether the estimated level of BNP exceeds a first threshold; and
- detecting an acute HF exacerbation based on whether the estimated level of BNP exceeds a second threshold.

12. The method of claim 1, wherein:
- steps (a), (b) and (c) are repeated from time to time;
- step (d) comprises monitoring changes in the patient's estimated level of BNP by monitoring changes in the at least one ventricular evoked response metric determined at step (c); and further comprising:
(e) monitoring the patient's heart failure (HF) condition based on the changes in the patient's estimated level of BNP monitored at step (d).

13. The method of claim 12, wherein step (e) includes:
- detecting a worsening of the patient's HF condition if the patient's estimated level of BNP increases; and
- detecting an improvement of the patient's HF condition if the patient's estimated level of BNP decreases.

14. The method of claim 12, wherein step (e) includes at least one of the following:
- predicting an impending acute HF exacerbation based on whether the monitored change in the patient's estimated level of BNP exceeds a first threshold; and
- detecting an acute HF exacerbation based on whether the monitored change in the patient's estimated level of BNP exceeds a second threshold.

15. The method of claim 1, wherein step (d) comprises estimating a patient's level of BNP by estimating a value for the patient's level of BNP based on at least one ventricular evoked response metric determined at step (c); and
further comprising:
(e) monitoring for an acute myocardial infarction (MI) based on the patient's estimated level of BNP estimated at step (d).

16. The method of claim 15, wherein step (e) comprises at least one of the following:
- predicting an impending acute MI based on whether the estimated level of BNP exceeds a first threshold; and detecting an acute MI based on whether the estimated level of BNP exceeds a second threshold.

17. The method of claim 1, wherein:
steps (a), (b) and (c) are repeated from time to time;
step (d) comprises estimating changes in the patient's level of BNP based on monitoring changes in the at least one ventricular evoked response metric determined at step (c); and
further comprising:
(e) monitoring for an acute myocardial infarction (MI) based on the estimated changes in the patient's level of BNP monitored at step (d).

18. The method of claim 17, wherein step (e) includes:
detecting an increased risk of MI if the patient's estimated level of BNP increases; and
detecting a decreased risk of MI if the patient's estimated level of BNP decreases.

19. The method of claim 17, wherein step (e) comprises at least one of the following:
predicting an impending acute MI based on whether the estimated change in the patient's level of BNP exceeds a first threshold; and
detecting an acute MI based on whether the estimated change in the patient's level of BNP exceeds a second threshold.

20. The method of claim 1, wherein the at least one ventricular evoked response metric is selected from the group consisting of:
ventricular evoked response peak-to-peak amplitude;
ventricular evoked response area; and
ventricular evoked response maximum slope.

21. The method of claim 1, wherein the at least one ventricular evoked response metric is selected from the group consisting of:
ventricular evoked response maximum amplitude;
ventricular evoked response minimum amplitude;
ventricular evoked response timing;
ventricular evoked response maximum amplitude dispersion;
ventricular evoked response minimum amplitude dispersion;
ventricular evoked response peak-to-peak amplitude dispersion;
ventricular evoked response area dispersion;
ventricular evoked response slope dispersion; and
ventricular evoked response timing dispersion.

22. An implantable system for monitoring a patient's level of B-type natriuretic peptide (BNP), comprising:
a pulse generator, connectable to at least one implanted lead, and configured to provide pacing stimulation to at least one of the patient's ventricles;
a sensing circuit, connectable to at least one implanted lead, and configured to obtain a ventricular intracardiac electrogram (IEGM) indicative of a ventricular evoked response to at least one of the patient's ventricles being paced;
a ventricular evoked response monitor to determine, based on the ventricular IEGM, at least one ventricular evoked response metric indicative of the ventricular evoked response to at least one of the patient's ventricles being paced; and
a BNP monitor comprising a microprocessor programmed to monitor the patient's estimated level of BNP wherein the microprocessor is programmed to estimate the of BNP based on the at least one ventricular evoked response metric.

23. The implantable system of claim 22, further comprising:
a heart failure monitor to monitor the patient's heart failure (HF) condition based on the monitored estimated level of BNP.

24. The implantable system of claim 22, further comprising:
a myocardial infarction monitor to monitor for an acute myocardial infarction (MI) based on the monitored estimated level of BNP.

* * * * *